United States Patent [19]

Eldridge, Jr.

[11] 4,385,692
[45] May 31, 1983

[54] SURGICAL INSTRUMENT TIP PROTECTOR AND METHOD OF MANUFACTURE

[75] Inventor: John D. Eldridge, Jr., Balboa Island, Calif.

[73] Assignee: Instranetics, Inc., Tustin, Calif.

[21] Appl. No.: 264,115

[22] Filed: May 15, 1981

[51] Int. Cl.³ .................... B65D 81/02; A61B 17/06
[52] U.S. Cl. .............................. 206/363; 206/45.31; 206/523
[58] Field of Search ............... 206/363, 478, 45.31, 206/523; 229/68

[56] References Cited

U.S. PATENT DOCUMENTS

| | | | |
|---|---|---|---|
| 3,256,527 | 6/1966 | Studen | 206/523 |
| 3,432,380 | 3/1969 | Weber | 206/45.31 |
| 3,489,270 | 1/1970 | Bixler et al. | 206/45.31 |
| 4,142,632 | 3/1979 | Sandel | 206/478 |

*Primary Examiner*—William T. Dixson, Jr.
*Attorney, Agent, or Firm*—Knobbe, Martens, Olson & Bear

[57] ABSTRACT

A surgical instrument tip protector has a cushioned foam base member for receiving a surgical instrument positioned thereon and a cover member which overlies a lower portion of said base and is peripherally bonded to said base to form an open-ended pocket to protect the instrument tip. The cover is a single integrally formed material comprising a foam portion which is essentially opaque and a non-porous portion which is essentially transparent located to permit the visual inspection of said instrument tip. The cover is formed by providing a single piece of foam and applying heat and pressure to a predetermined area to form the non-porous transparent portion.

6 Claims, 5 Drawing Figures

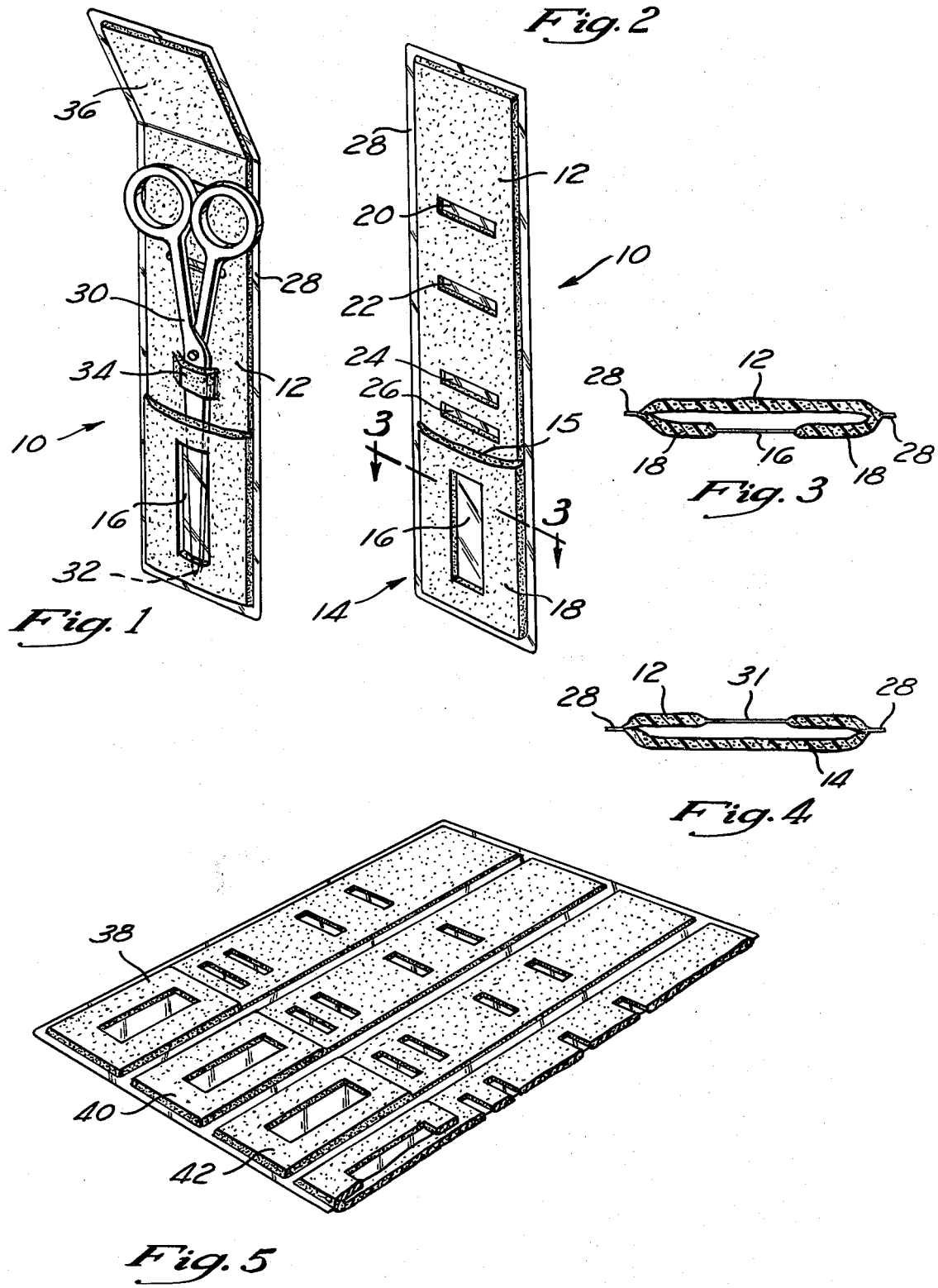

SURGICAL INSTRUMENT TIP PROTECTOR AND METHOD OF MANUFACTURE

BACKGROUND OF THE INVENTION

The present invention generally relates to devices for holding surgical instruments and more specifically to devices which also protect the tips of such instruments while providing visual inspection of said tips.

Surgical instruments must be sterilized before use in the operating room. Commonly such instruments are placed in plastic packages and submitted to steam or gas sterilization as is well-known.

Transparent plastic envelopes allow surgical personnel to identify the type of instrument. Such identification is often made through examination of the tip since instruments may differ significantly only with respect to the tip. However, problems have resulted in the past since many of these surgical instruments have sharp tips which tend to puncture any non-rigid container such as the plastic envelopes. If such puncture occurs the instrument may no longer be sterile, is subject to damage and is a health hazard to surgical personnel. Moreover, the plastic envelopes do not provide adequate protection to the instrument from impact and particularly the instrument tip itself.

In an attempt to solve these problems, one type of prior device is composed of a plurality of polyester foam pockets in side-by-side relation. An instrument is placed within each pocket. The foam of the backing member which extends above the pocket can be folded down to cover the upper portions of the retained instruments. The entire device may be rolled up if desired. Although this product offers puncture resistance and protection from impact, it does not permit the visual inspection of the instrument tip. In order to identify the instrument, hospital personnel must label each protective pouch with the name of the particular instrument. This procedure makes it awkward to reuse the device since each labeled pouch must be reused with the same type of instrument that was previously retained and sterilized.

Another prior device is the subject of U.S. Pat. No. 4,142,632, issued to Sandal. The Sandal device consists of a non-reticulated foam backing member of relatively small pore size for receiving a surgical instrument. Overlying and peripherally bonded to at least a portion of this member is a pouch which is composed of a reticulated foam having a very coarse pore size to allow visual inspection of the tip. While the Sandal device is satisfactory in many applications it suffers from a number of disadvantages. First, the pore size of the pouch member is so large, the sharp small tips of instruments can protrude through the foam. Secondly, the pouch member is of a density which does not allow clear visual inspection of the instrument tip. Thirdly, the instrument can easily catch on the mesh as it is being placed in the pouch which can be a nuisance to operating room personnel.

Thus, there remains a definite need for an instrument tip protector which provides puncture resistance to the instrument tip, protects the instrument from impact and permits the clear, accurate visual inspection of the instrument tip.

SUMMARY OF THE INVENTION

The present invention obviates the disadvantages of prior devices and possesses the necessary attributes discussed above. The device has a first foam section which forms a cushioned surface for receiving a surgical instrument. In order to form a cover for the first section, heat and pressure are applied to a predetermined area of a second foam section which destroys the porosity in that area creating an essentially transparent window surrounded by foam. A portion of the periphery of the second section is then bonded to the lower portion of the first section to form an open-ended pocket for receiving the tip of the instrument.

Since the device is essentially composed of a foam padding, it provides substantial resistance to puncture by the instrument tip and also acts as a cushion to protect the instrument from impact. Moreover, the transparent area allows clear visual identification of the tip.

The second section is therefore a single integrally formed material which offers all of the advantages of a non-reticulated finely celled foam, i.e., protection and puncture resistance while still allowing clear identification of the instrument tip. Being an integral section, the second section has no internal seams around the window which could be broken by sterilization of the instrument itself. Moreover, it is manufactured simply and economically.

These and other advantages will be discussed below with reference to the following drawings in which:

FIG. 1 is a perspective view of the instrument tip protector shown holding a surgical scissors;

FIG. 2 is a perspective view of the instrument tip protector ready to receive an instrument;

FIG. 3 is a sectional view taken through line 3—3 of FIG. 2;

FIG. 4 is a sectional view taken through line 3—3 of an alternate embodiment having the window portion on the base member;

FIG. 5 is a perspective view of an alternate embodiment showing a plurality of instrument tip protectors in side-by-side relation.

PREFERRED EMBODIMENT

Referring to FIGS. 2-3, a device 10 is shown generally comprising a rectangularly shaped base member 12 and a cover member 14 overlying the lower portion of said base member 12. The cover member 14 has an essentially transparent window portion 16 which is surrounded by a protective portion 18.

In the preferred embodiment, the width of the cover member 14 is essentially the same as that of the base member 12, but the length of the cover member 14 is only about one-third that of the base member 12. Thus, the cover member 14 overlies only about the lower third of the base member 12. The perimeter of the cover member 14, except a top side 15, is bonded to the base member 12. The cover member 14, therefore, forms an open-ended pocket with the lower portion of the base member 12.

The surface area of the window portion 16 is substantially less than the surface area of the entire cover member 14. In the preferred embodiment, the window portion 16 is ¾ inch wide by one and one-half inches long and the protective member 18 is about one and three quarter inches wide by two and one-half inches long. Thus, in the preferred embodiment, the window portion 16 has about one fourth the surface area of the entire cover member 14.

The base member 12 has longitudinally spaced depressed areas 20, 22, 24, 26 located above the cover member 14. A thin border 28 completely surrounds the device 10.

Referring to FIG. 1, the base member 12, in the preferred embodiment, is formed of a foam having a relatively small pore size. The foam base member 12 serves as a cushioned surface for receiving a surgical instrument, such as a scissors 30 having a sharp tip 32. The fact that the foam has fine pores prevents the sharp tip 32 of the scissors 30 from protruding through or puncturing the base member 12. The foam is soft and has sufficient thickness to provide substantial protection to the instrument 30 from impact. In the preferred embodiment, the base member 12 is about 7/32 inch thick. A foam which has been found satisfactory is a polyurethane foam manufactured by Crest Foam Company, 100 Carol Place, Moonachie, New Jersey. This foam has about 70-80 pores per sq. inch. Other types of foam which have high resistance to the extreme temperatures of hospital sterilization procedures would be adequate.

The protective portion 18 is also formed of a foam having a relatively fine pore size. Advantageously, the protective portion 18 may be formed of the same foam as the base member 12. In the preferred embodiment, the protective portion 18 is about ⅛ inches thick which is slightly thinner than the foam of the base member 12.

As shown in FIG. 1, the protective portion 18 covers the sharp tip 32. The foam pocket formed by the lower portion of the base member 12 and a cover member 14 protects the instrument tip 32 from damage due to physical impact and also prevents the tip 32 from puncturing the device 10.

The window portion 16 is a thin sheet of transparent material. The window portion 16 is somewhat wider than the instrument tip 32 and is long enough to cover a substantial portion of the lower section of the instrument 30. Thus, the window portion 16 is sized to allow hospital personnel to easily and clearly identify the instrument 30 by viewing its working portion.

The window portion 16 has a smooth surface which permits the instrument 30 to be easily slid into the protective pocket 18 without snagging.

In short, the device 10 provides substantial protection to the instrument 30, provides high resistance to puncture from the instrument tip 32 and permits hospital personnel to clearly and easily identify the instrument by viewing the lower portion of the instrument 30.

In the preferred embodiment, the window portion 16 is transparent and is formed of the same polymer which forms the protective portion 18. As will become clear from its method of manufacture which will now be described, the cover member 14 is advantageously a single integrally formed material.

To manufacture the cover member 14, a foam section is provided which, in the preferred embodiment, is formed from the same foam as the base member 12. It, therefore, has a relatively fine pore size. Thus, the cover member 14 begins as a single integral piece of foam having no window portion 16.

Heat and pressure are then applied to an area of the foam of a size and location predetermined to produce the window portion 16. The heat and pressure compresses the area into a thin, tough, essentially transparent film. The heat and pressure are applied in a compression die. In the preferred embodiment, about 1700 PSI are applied at about 400° F. This method destroys the porosity of the foam in that area which substantially reduces the refraction of light and therefore, the non-porous area is essentially transparent.

Since the cover member 14 is formed of a single, integral piece of material, there are no seams between the window portion 16 and protective portion 18 which could break due to pressure from the instrument 30 from sterilization procedures. Moreover, since the window portion 16 contains the same amount of material in a highly compressed state, the window portion 16 is stronger and more resistant to puncture than the protective portion 18. The protective portion 18 is important since it provides cushioned protection for the instrument from impact. Thus, the cover member 14 allows easy clear identification of the instrument 30 while still providing cushioned protection from impact and is formed in a simple, one step process.

FIG. 4 depicts a sectional view through line 3—3 of FIG. 2 of an alternate embodiment. As shown, a window 31 like the window portion 16 could be formed in the lower portion of the base member 12. The size of the window 31 as well as its location relative to the working portion of the instrument 30 would be analogous to the window portion 16. Advantageously, the window 31 in the base member 12 would be formed by heat and pressure in the same one step manner as described with respect to the formation of the window portion 16. It should be understood that the window 31 in the base member 12 could take the place of or be in addition to the window portion 16 in the cover member 14.

The depressed areas 20, 22, 24, 26 are formed by applying heat and pressure to the foam of the base member 12.

The cover member 14 is affixed to the base member 12 by placing the lower portion of the base member 12 over cover member 14 and applying heat and pressure to the peripheral boundary of the cover member 14 except the top side 15. If the base and cover members 12, 14 are formed from a single foam, the cover member 14 is folded upward over the base member 12 and then bonded thereto as described. As shown clearly in FIG. 3, the heat and pressure seals the periphery of the cover member 14 to the underlying periphery of the base member 12 and forms the single thin border 28. If desired, heat and pressure can be applied to the entire perimeter of the base member 12 to form the thin border 28 entirely around device 10.

The areas 20, 22, 24, 26 are precut with a die to form a narrow slit (not shown) in each area. When the areas 24, 26 are severed in this manner, the area of foam located between the areas 24, 26 can be formed into a loop 34 shown in FIG. 1.

To employ the device 10, the instrument tip 32 is threaded through the loop 34 from above. The scissors 30 are moved downward so that the tip 32 enters the opening between the base member 12 and the top side 15 of the cover member 14. The sliding action continues until the tip 32 reaches the bottom of the pocket formed by the base and cover members 12, 14. The loop 34 prevents the instrument from shifting or becoming dislodged from the pocket.

Once the instrument 30 is in place, the device 10 can be placed in a plastic bag or other suitable container and sterilized by well-known gas or steam procedures. Due to the window portion 16, hospital personnel are able to identify the instrument without opening the plastic bag. This is an important advantage since if the bag were opened the instrument would no longer be sterile. In the prior device shown in U.S. Pat. No. 4,142,632, clear identification is difficult through the reticulated coarse foam. Moreover, as discussed in the background section above, the device which permits identification of the instrument through labeling makes reuse of the device awkward.

Advantageously, the base member is substantially larger than the instrument 30 so that its extreme upper portion 36 shown in FIG. 1 can be folded down over the top of the instrument handle to provide additional protection and help retain the instrument within the pocket.

Referring to FIG. 5, another embodiment is shown comprised of a plurality of instrument holders, 38, 40, 42 arranged in a side-by-side relation. The holders 38, 40, 42 are essentially identical to the device 10, except that adjacent holders share a common border formed by heat and pressure, as described with respect to the border 28 of FIGS. 1-3. The embodiment of FIG. 5, is therefore, capable of holding multiple instruments and can be rolled up into a highly protective roll.

I claim:

1. A sterilizable protector for a surgical instrument comprising:

a base member being formed of heat sterilizable fine-pore foam upon which said instrument rests; and an integral cover overlying a portion of said base member and having a periphery, a portion of which is bonded to said member and a top portion of which is unbonded to form an open-ended pocket for said instrument tip, said cover having a cushioned portion being formed of heat sterilizable fine-pore foam and a puncture resistant transparent window portion to permit identification of said instrument, said window portion being formed of pressed and heated heat sterilizable fine-pore foam.

2. A sterilizable protector for a surgical instrument comprising:

a protective impact resistant surface being formed of fine-pore polyurethane foam upon which said instrument rests; and a cover overlying a portion of said surface and peripherally bonded to said surface forming an open-ended pocket for receiving the tip of said instrument, said pocket being formed of fine-pore polyurethane foam and having an impact resistant portion which is essentially opaque, and an essentially non-porous, puncture resistant, transparent film portion formed by pressed and heated fine-pore polyurethane foam, which permits identification of said instrument.

3. A process for manufacturing a sterilizable surgical instrument tip protector comprising:

providing a section of heat sterilizable fine-pore foam;

applying heat and pressure to a predetermined area of said foam to make said area transparent and puncture resistant;

providing a second member of heat sterilizable fine-pore small-pore polyurethane foam;

affixing said section of foam to said second member to form a pocket which is capable of holding a surgical instrument tip, said transparent area being positioned to permit visual inspection of a lower portion of the instrument.

4. The product produced by the process of claim 3.

5. A process for manufacturing a sterilizable surgical instrument tip protector comprising:

providing a piece of small-pore polyurethane foam;

applying heat and pressure to a predetermined area of said foam to make said area transparent and puncture resistant;

folding said foam into a first section and a second section overlying a portion of said first section; and bonding a portion of the periphery of said second section to said first section to form a pocket to receive said instrument tip, the unbonded portion of the periphery forming an open-end to permit entry of said instrument between said first and second portions.

6. The product produced by the process of claim 5.

* * * * *